United States Patent [19]
Wang

[11] Patent Number: 5,939,380
[45] Date of Patent: Aug. 17, 1999

[54] IMPLANT PREPARATIONS CONTAINING BIOACTIVE MACROMOLECULE FOR SUSTAINED DELIVERY

[76] Inventor: Paul Yao-Cheung Wang, 47 Marblemount Crescent, Agincourt, Ontario, Canada, M1T 2H5

[21] Appl. No.: 07/796,023

[22] Filed: Nov. 22, 1991

Related U.S. Application Data

[60] Division of application No. 07/063,968, Jun. 19, 1987, Pat. No. 5,110,595, which is a continuation-in-part of application No. 07/016,845, Feb. 20, 1987, abandoned.

[30] Foreign Application Priority Data

Feb. 18, 1987 [CA] Canada ...................................... 509526

[51] Int. Cl.⁶ ........................... A61K 9/22; A61K 38/27; A61K 38/28; A61K 47/44
[52] U.S. Cl. ............................. 514/2; 424/426; 424/468; 424/484; 514/3; 514/21; 514/964
[58] Field of Search ............................. 514/4, 3, 2, 964, 514/14, 21; 424/468, 426, 484

[56] References Cited

U.S. PATENT DOCUMENTS

| | | | |
|---|---|---|---|
| 4,452,775 | 6/1984 | Kent | 514/3 |
| 4,579,730 | 4/1986 | Kidron et al. | 514/3 |
| 4,775,659 | 10/1988 | Thakkar et al. | 514/964 |
| 4,837,381 | 6/1989 | Steber et al. | 514/2 |
| 4,882,167 | 11/1989 | Jang et al. | 424/468 |

FOREIGN PATENT DOCUMENTS 143949   6/1985   European Pat. Off. ................... 514/2

OTHER PUBLICATIONS

Absorption Rate of Hormone–Cholesterol Pellets, by Shimkin et al., Edocrinology, 29, (1941), 1020–1025.
Sustained Release Hormonal Preparations, by Kinel et al., Acta Endocrinologica, 64, (1970), 253–264.
The Effect of Dose and Nutritive State of the Renotrophic and Androgenic Activities of Various Steroids, by Kochakian, Am. J. Physiol. 145 (1945), 549–556.
Sustained–Release Hormonal Preparations XV: Release of Progesterone Pellets In Vivo, by Joseph et al., J. Pharm. Sci, 66 (1977), 490–493.

*Primary Examiner*—Jeffrey E. Russel
*Attorney, Agent, or Firm*—Ostrolenk, Faber, Gerb & Soffen, LLP

[57] ABSTRACT

Implant preparations capable of sustained action when inserted are comprised of powder of a natural lipoidal substance in thorough admixture with bioactive macromolecule, followed by compression under pressure into a disc or rod that can be broken and used in small pieces as well.

17 Claims, No Drawings

IMPLANT PREPARATIONS CONTAINING BIOACTIVE MACROMOLECULE FOR SUSTAINED DELIVERY

This is a division of application Ser. No. 07/063,968, filed Jun. 19, 1987, now U.S. Pat. No. 5,110,595, which was a continuation-in-part of application Ser. No. 07/016,845 filed Feb. 20, 1987 and now abandoned.

FIELD OF THE INVENTION

This invention relates to bio-absorbable implant preparations containing a bioactive macromolecule, which are capable of sustained action when implanted.

BACKGROUND OF THE INVENTION

Drug administration by the oral route is applicable mostly to low molecular weight (<850 daltons) compounds which are relatively stable at the acidic pH of the stomach and the alkaline condition of the gastrointestinal tract. Bioactive macromolecules, such as insulin (Mol. Wt. 6,000 daltons) which promote growth and control blood sugar level, and the growth hormone somatotropin (Mol. Wt. 22,000 daltons) or the like are inactivated by proteolytic enzymes in the digestive tract, if taken by mouth. As a result, these bioactive macromolecules can be administered only by injection. However injection usually introduces too high an initial dose which is absorbed in part as well as degraded by serous enzymes at the subcutaneous injection site resulting in rapid decay to an inadequately low level a few hours later. To compensate for the decay, a second injection is required. Another remedy to correct the inconsistency is to infuse a dilute solution of the labile agent continuously at a low rate. The slow infusion can actually achieve a better outcome, because most active agents have a relatively short half-life in vivo or are toxic if the daily required dose is given at once by injection. However, the advantage of low-dose infusion is compromised by the incidence of infection and discomfort due to the presence of the indwelling needle and the catheter attachment. Therefore, extensive effort is continuing to find an implantable infusion device or preparation that can deliver an active agent for a prolonged period of time.

BRIEF REFERENCE TO THE PRIOR ART

In the early 1970's when the merit of giving a drug in small doses by continuous external infusion was demonstrated, further efforts were aimed at the development of implantable pumps and drug releasing capsules to simulate the functions of organs such as the hormone secreting endocrine glands. Another purpose was to free the recipient of the chance of infection and provide total unrestrained mobility which often contributed immensely to the patient's sense of well being.

There is one implantable pump available commercially at present (the Infusaid® Implantable Pump manufactured and marketed by the Infusaid Corporation, Norwood, Mass.). This titanium device weighs about 200 g, has a drug solution reservoir capacity of about 40 mL and is powered by a volatile fluorocarbon propellant which exerts a constant pressure on the collapsible drug solution reservoir. The liquid is driven through a length of resistive capillary coil to deliver the solution at a flow rate of about 5 mL/day. In about a week, the reservoir must be refilled percutaneously, and drug spilling into the subcutaneous space occurred frequently. Further, this implantable pump can be used only with active agents that are soluble in aqueous buffer solutions, stable at body temperature, and do not form aggregates which will clog the filter or the flow-regulating resistive capillary of the pump.

In the past six years, experience has shown that this device works relatively well with low molecular weight drugs, such as morphine (Mol. Wt. 285), 2'-deoxy-5-fluorouridine (Mol. Wt. 246) or the like in the treatment of cancer patients at a relatively advanced state of the disease. For macromolecular weight drugs, this pump also works quite well with the heparin anticoagulant; however, polypeptide hormones, such as insulin and somatotropin or the like, have limited solubility and have a high tendency to form aggregates after a few days in solution. Therefore, the implantable pump is not suitable for these polypeptide hormones.

There have been several different designs of implantable pumps under development during the past five years. These experimental prototypes all use electrically powered roller pumps to propel the liquid from the solution reservoir. Because the maximum size of a subcutaneous implant is about 9 cm in diameter by about 3 cm in thickness, the space taken up by the electrical and mechanical components forced the reduction of the reservoir volume to less than 30 mL, which necessitates more frequent refilling. Further, moisture penetration due to sealing defects of the metallic enclosure often led to short circuiting and pump failure. Therefore, despite extensive effort over the past several years, the Infusaid® implantable pump remains the only one commercially available. It is apparent that drug delivery by implantable pumps has reached close to the limit of feasibility.

In a quite different approach, many existing and specially synthesized polymers have been evaluated for suitability as excipient for drug delivery implants. The advantages of such an implant are its relatively small size as compared to the pumps aforementioned, and the fact that the active agent can be compounded with the excipient material directly in an amount without dilution which often lasts for months or even years. The implant which has received extensive evaluation is the contraceptive silicone capsule containing norgestrel having a molecular weight of 312 daltons. This low molecular weight steroid can penetrate the silicone material continuously to prevent pregnancy for up to 5 years (H. B. Croxatto, et al., Contraception, 23, 1981, 197). However, the fibrous tissue encapsulation developed in time around the implant makes its removal extremely difficult. For this reason, and also because bioactive macromolecules cannot penetrate the silicone rubber, further efforts have been directed at the development of excipients that can be eroded and gradually absorbed in the body (J. Heller in Recent Advances in Drug Releasing Systems, Anderson & Kim (eds) Plenum Press, 1984, N.Y., p.101). The erosion will also allow the leaching out of the bioactive macromolecule incorporated therein, and make the removal later unnecessary.

Several synthetic polymers, notably poly-(alkyl-$\alpha$-cyanoacrylate), polyurethanes, and polyesters are known to degrade to some extent and become absorbed once implanted in the body. However, because of the limited possibility of controlling the biodegradation rate as well as the toxic degradation products formed, especially by poly-(alkyl-$\alpha$-cyanoacrylate) and polyurethane, the current search for a biodegradable drug delivery implant has concentrated almost exclusively on different kinds of polyester as the excipient material. Often, the novel polyesters erode too slowly in the aqueous environment, and as a result even low molecular weight drugs become entrapped therein. Therefore, these excipients are not useful for delivery of bioactive macromolecules. It is then necessary to incorporate latent catalyst additives with the excipient to enhance hydrolysis in order to free the entrapped drug. Not to mention the biological consequences, the additives and the fragments formed by the depolymerization of the polyester will limit the number of drugs that can be compounded with the excipient materials. The limitation seriously reduces the general usefulness of these polymers as a potential excipient for drug delivery implants. Consequently, in spite of extensive efforts, very few such experimental implants have advanced even to the level of testing in laboratory animals.

At present, there is only one procedure producing a non-absorbable polymer implant for polypeptide hormone such as insulin which has been clearly demonstrated to be capable of promoting growth and reducing hyperglycemia for many weeks (Langer et al., Diabetes, 29 (1980) 37). In this procedure, insulin is mixed with poly-(ethylene/vinyl acetate) copolymer in methylene chloride at sub-zero temperature, and the solvent is then slowly evaporated. The resulting slab can be seen under the electron microscope to contain small pores which allow the diffusion of insulin from the polymer implant. Even with this special elaborate process, only about 3% of the insulin incorporated will become available for reducing hyperglycemia. Since the small pores may be prone to clogging, and the poly-(ethylene/vinyl acetate) copolymer is not degraded in the body, the majority of the insulin is trapped by the solid polymer phase without being able to exert its activity. Although the procedure is a remarkable advancement in the technology of sustained action implants for insulin, the preparation does not have much practical significance.

In consideration of the aforementioned, an implant containing bioactive macromolecule should be simple, so that it will be easy to fabricate and require no follow-up maintenance when implanted. Its size has to be small to avoid imposing excessive tension on the subcutaneous tissue due to stretching when the implant is inserted in the body. The device should be able to hold a sufficient amount of the active protein to sustain the desired therapeutic effect for many weeks. As well, the excipient component should be absorbable by the body without adverse effect, so that no time consuming surgical procedure is needed to explant the depleted device. Further, when the implant stops functioning after several weeks, the incorporated active ingredient should be essentially depleted, so that a new absorbable implant can be inserted, if desired, to continue the therapeutic regimen without any interference from residual activity of the previous implant. Finally, it is equally important that no surge of the active ingredient should occur in the body that could cause an overdose and be dangerous to the recipient, if the implant is fractured.

SUMMARY OF THE INVENTION

It is an object of the present invention to provide absorbable preparations containing a bioactive macromolecule capable of sustained release for many weeks.

It is a further object of the present invention to provide preparations containing polypeptide hormone for reduction of hyperglycemia and growth promotion which satisfy one or more of the above criteria.

The present invention provides preparations containing a bioactive macromolecule and an essentially water-insoluble compound in the form of lipoidal fatty substances as the excipient. When implanted, the desired effect is achieved, and at the same time the said lipoidal excipient can be absorbed as well as used by the body without adverse effect.

In one embodiment, the excipient in admixture with bioactive macromolecule is compressed into a pellet disc or rod, and a portion thereof is implanted subcutaneously to achieve the desired effect for many weeks. In another embodiment, the pellet disc made of a lipid and bioactive macromolecule is broken up into chips, and a suitable amount is inserted subcutaneously through the lumen of a large gauge hypodermic needle.

Like other materials aforementioned, lipids have been used to deliver low molecular weight compounds, such as steroid hormones (Kincl, et al., J. Pharm. Sci., 66, (1977), 490). These lipoidal substances, being components of all animal cells and tissues, are varieties of water-insoluble compounds. The most abundant kind is the glycerides which can be hydrolyzed to yield long-chain fatty acids of negligible water-solubility. When these long-chain acids are esterified with their alcohol derivatives, they form waxes which serve as a protective coating of the surface tissues. Other members of the saponifiable lipid family are phospholipids and the sphingolipids found mostly in cell membranes. Among the non-saponifiable lipids, terpenes and most steroids are two important classes. In addition, some steroid-like vitamins are sometimes classified as lipoidal fatty substances. The most abundant steroid is cholesterol, which is also found in body fluids in combination with long-chain fatty acids.

For use in the present invention, lipoidal substances which are solid at room temperature are selected and made into powder form without any other special treatments aside from grinding in a mortar and pestle for a few minutes. The lipid powder is simply admixed with a suitable amount of bioactive macromolecule, and compressed into a disc or rod without any other components. Typical of such solid lipids are saturated fatty acids with 12 or more carbon atoms in the linear chain. The preferred fatty acids are lauric, myristic, palmitic, and stearic acids or a combination of these acids. Their glycerides, as well as similar esters of their unsaturated equivalents, are also solids and readily available in abundance. However, the esters of these long-chain acids and their corresponding alcohols are sometimes waxy substances which may be hardened and ground at low temperature into the powder form. Polar lipids that can be considered as well include phosphatidylethanolamine, phosphatidylcholine, sphingomyelin, phosphatidylserine, phosphatidylinositol, cardiolipin, galactocerebroside, glucocerebroside or the like. Among the solid steroid or steroid-like members of the solid lipids, the carotenes, vitamins D and K, cholic acids, coprostanol, and cholesterol are readily available in the powder form. The preferred steroidal lipid is cholesterol which is practically insoluble in water, can be readily compressed into a coherent mass without any binder, and is not known to have any pharmacological effect in the body or be deleterious to bioactive macromolecule. It is thus also suitable as an excipient to be used in the instant invention.

In making the pellet disc or rod, all that is required is to admix a dry lipid powder thoroughly with a bioactive macromolecule, and then compress the resulting admixture in a die. If the lipid powder is merely melted down, suspended or dissolved in a solvent followed by evaporation to form a slab, the powder of bioactive macromolecule will not disperse evenly with the lipoidal excipient which will also be brittle and fragile to handle. The uneven dispersion may also cause too much of the bioactive macromolecule to be available at one time or too little at another after implantation. Further, when chips are to be obtained, cutting often leads to excessive fracture or disintegration of the slab made by melting or solvent casting. There is also the possibility of inactivation of the bioactive macromolecule by heating or organic solvent action. However, a pellet disc made by high pressure compression of the said dry powder admixture at room temperature can be readily cut with a sharp blade into approximately 1 mm$^3$ pieces.

In one embodiment, the preparation is made by adding about 8.5 parts of a natural lipoidal compound to 1.5 part of a desired bioactive macromolecule. The powder admixture in a capped plastic vial is further placed on a vortex mixer to ensure thorough mixing, and then carefully transferred into the well of a 13-mm pellet die to yield a smooth and firm pellet disc after compression at 2.5 metric tons.

In a preferred embodiment of the present invention, 8 parts of palmitic acid powder is mixed thoroughly on a vortex mixer with 2 parts of powder of a bioactive macromolecule. The powder admixture is compressed at 5 metric tons into a pellet disc, as aforementioned, having a total weight of about 200 mg.

In still another embodiment of the present invention, the standard size pellet disc containing a bioactive macromolecule is cut into chips of approximately 1 mm$^3$ in size by a sharp blade. These chips are small enough to be pushed into the subcutaneous space through the lumen of a trocar needle, thus avoiding the need for implantation by a skin incision as required in the case of the disc.

The pellet discs or the chips thereof, made as just described, will release only a negligible amount of a water-insoluble bioactive macromolecule such as insulin, when immersed in a buffer solution even over a period of several months. Otherwise, the delivery rate may be assessed in vitro. Scanning electron microscopy shows that the high compression used to make the pellet disc has fused the powders into layers of coherent solid mass. However, once implanted, the desired pharmacological effect of a bioactive macromolecule can be readily observed, because the lipoidal material, though insoluble in water, is nevertheless a component of cell as well as tissue, and thus can be gradually eroded in vivo. Therefore, the appropriate amount of insulin required daily from the pellet disc of the present invention to lower hyperglycemia to an acceptable level while promoting growth may be determined to some extent by trial in vivo using different sizes of the insulin containing disc. If a lesser amount of the insulin daily is desired, it can be achieved by implanting a small piece of the standard size pellet disc which is 13-mm in diameter and 1.5 mm thick. Otherwise, a slightly larger piece may be used to provide more insulin daily, if required. The factors which determine the efficacy of the insulin available from the implantable preparation of the present invention are very complicated and cannot be attributed to release from the implant by simple diffusion. It is found that when 50-mg fragment of a 200-mg pellet disc with less than 10% insulin in the lipoidal excipient is used, the implant shows no effect at all or only occasionally reduces hyperglycemia slightly for a short few days, which is impractical. When much more than 30% insulin is present therein, the implant may be fatal to the diabetic test animal or again, the reduction in hyperglycemia occurs for only several days. The less than optimal performance may be due to other biological parameters, such as the rate of insulin absorption by tissue, its inactivation by antibodies and enzymes in interstitial fluids, fluctuating metabolic demands, etc., that cannot be overlooked. Because of the variable biological parameters just aforementioned, it is often observed that, for example with 20% insulin content, very similar level and length of time in hyperglycemia reduction and body weight gains can be achieved when the 1-mm$^3$ chips equivalent in weight to a quarter piece disc, a ⅛ or ¼ piece of the whole pellet disc is implanted. In contrast, when identical pieces of the insulin containing implant were inserted in several diabetic animals of comparable body weight, the length of time observed for hyperglycemia reduction and increase in body weight may be different. But, subcutaneous insertion of three ¼ pieces of an active pellet disc is generally found to be fatal for a diabetic Wistar rat of body weight <400 g. Therefore, in spite of these biological variations, it is possible to determine a suitable implant size by the bioassay method just described which will result in effective reduction in hyperglycemia while sustaining growth for several weeks at least, and often exceeding 1 month.

The amount of insulin can be about 11% to about 40% by weight, and the amount of somatotropin can be about 1% to about 50% by weight.

The invention is further described by the following specific examples, which are presented as illustrations, and not intended to limit the scope of the present invention.

EXAMPLE 1

An amount of 160 mg of powdered palmitic acid and 40 mg of powdered bovine insulin (24 IU/mg) are first mixed by hand in a 4 cm by 4 cm plastic weighing boat using a stainless steel spatula. The mixed powder is then transferred into a 1.5-mL capacity conical centrifuge tube with cap, which is made of polyethylene material. The capped conical vial is pressed onto the platform of a vortex mixer (Vortex-Genie Mixer Catalogue number 12-812, Fisher Scientific Co., Toronto) turned to its maximum speed. After 2 min on the mixer, all the well-mixed powder is carefully tapped from the vial into the well of the Spex 13-mm die (Spex Industries, Inc., Edison N.J.). When the plunger component is properly lowered into the well, the die set is placed in the centre between the jaws of the hydraulic press (Spex-Carver Model C, Spex Industries, Inc.). A moderate compression of 0.5 metric ton is first applied before the vacuum pump hose is connected to the side of the die set to evacuate its internal chamber. After 2 min. of evacuation to remove entrapped air which would make the interior porous and reduce cohesion, the compression is raised to 5 metric tons and held at this level for 5 min. When the vacuum and compression are released, the mid section of the die housing is unscrewed from its base and the finished pellet disc is pushed from the central well by gently tapping the exposed plunger stem.

The smooth opaque pellet disc is scored in the middle with a small nail file before it is cut into 2 equal pieces over the groove with a utility knife. One ½ piece of the pellet disc and a plastic coated magnetic stirring bar are dropped into 100 mL of phosphate buffered saline at pH 7.4 in a 300-mL flask which can be closed with a screw cap. The content of the flask is stirred gently at room temperature and 0.8 mL of the solution is taken weekly. The solution sample is mixed with 0.2 mL of a Coomassie G-250 dye reagent (Protein Assay Kit, Cat. No. 500-0006, Bio-Rad Laboratories, Ltd., Mississauga, Ontario) and the intensity of the blue-green color is measured at 595 nm. This method has a sensitivity of 1 $\mu$g protein/mL and is highly reproducible. Analyses over a 6-week period show that less than a total of 10 $\mu$g insulin has leached out, which ensures that no initial burst of the drug will occur upon implantation to cause any dangerous overdose.

TEST 1

Male Wistar rats weighing 320 to 380 g each are divided into 3 groups with 1 as healthy control, a second one as diabetic control and a third group of 2 for testing. Each animal in the second and third group is injected with 50 mg streptozotocin/kg body weight by the tail vein to induce diabetes by irreversibly destroying the insulin producing cells in their pancreas (O. P. Ganda, et al., Diabetes, 25, (1976), 595). A drop of blood is taken by tail vein puncture from each of the lightly ether-anesthetized animals and smeared evenly over the tip of the Dextrostix® (blood glucose test strip made by Miles Lab. Ltd., Etobicoke, Ontario). Meanwhile, the timer on the Glucometer® (Colorimeter for Dextrostik®, Miles Laboratories) is activated, and after 60 sec when the alarm has sounded, the blood layer is thoroughly washed off from the Dextrostix®. The intensity of the blue color on the tip is a measure of the blood glucose level in the sample and can be determined quantitatively by inserting the developed Dextrostik® into the Glucometer®, which will show the glucose content on its indicator display in mM glucose/L blood. The results show that the healthy control has a range of about 6–11 mM glucose/L blood, while the diabetics have a value exceeding 22 mM/L on the day after streptozotocin injection, which is the maximum limit that can be read on the Glucometer®. On the 8th day after the induction of hyperglycemia, 1 of the diabetic animals in the third group is implanted subcutaneously near the abdomen with ⅛ of the standard size pellet disc prepared as just described. A diabetic rat of body weight between 300–400 g requires about 3 IU insulin daily to lower the blood glucose level to the normal range of 6–11 mM/L. In the ⅛ portion of the standard size pellet disc, there is 5.0 mg insulin or a total of 120 IU, which should be sufficient to supply the need for 40 days. The remaining diabetic animal in the third group is implanted subcutaneously with ¼ of the standard size pellet disc. The ¼ disc contains enough insulin to reduce hyperglycemia for 80 days or almost 3 months. The blood sugar level for all 3 groups is monitored at convenient intervals henceforth. While the blood sample is being taken from the lightly anesthetized animal, the presence of the implanted discs is checked by palpation and the weight of the animal is also recorded. Food and water are made available to all the animals ad libitum. The blood glucose results are summarized in Table 1 shown below.

TABLE 1

Lowering of Blood Glucose by Insulin Containing Preparation Implanted in Diabetic Wistar Rats

| Duration | Blood Glucose (mM/L) | | | |
|---|---|---|---|---|
| | 1st Group | 2nd Group | 3rd Group | |
| (days) | (Healthy Control) | (Diabetic Control) | A* | B** |
| 0 | 9.1 | >22 | >22 | >22 |
| | | | Implanted | |
| 1 | 8.2 | — | 3.5 | 2.4 |
| 3 | — | — | 4.0 | 3.9 |
| 5 | 7.4 | >22 | 2.2 | 3.0 |
| 8 | — | — | 3.0 | 3.1 |
| 10 | 6.5 | — | — | — |
| 12 | 5.1 | >22 | 3.3 | 3.5 |
| 14 | — | — | 3.7 | 3.2 |
| 16 | — | — | 3.0 | 2.2 |
| 18 | 6.0 | — | 4.1 | 3.0 |
| 20 | — | >22 | — | — |
| 22 | 5.7 | — | 6.5 | 3.3 |

TABLE 1-continued

Lowering of Blood Glucose by Insulin Containing Preparation Implanted in Diabetic Wistar Rats

| Duration | Blood Glucose (mM/L) | | | |
|---|---|---|---|---|
| | 1st Group | 2nd Group | 3rd Group | |
| (days) | (Healthy Control) | (Diabetic Control) | A* | B** |
| 24 | — | — | 3.5 | 3.0 |
| 26 | 10.2 | — | — | 2.7 |
| 28 | — | — | 2.9 | 2.0 |
| 30 | 6.1 | >22 | 3.7 | 3.5 |
| 32 | — | — | 20.1 | 4.0 |
| 34 | 8.8 | — | >22 | 3.6 |
| 36 | — | — | 20.6 | 4.1 |
| 38 | 5.9 | >22 | >22 | 3.0 |
| 40 | — | — | — | 14.5 |
| 42 | — | — | — | >22 |
| 44 | — | >22 | — | >22 |
| 46 | — | — | >22 | >22 |
| 50 | 6.5 | >22 | — | >22 |

*⅛ disc
**¼ disc

As shown in the last 2 columns of Table 1, reduction in the blood glucose level was observed the next day indicating the fast onset of action. The test animals also continued to gain weight when checked at the time of taking blood samples. In the 30-day period, the diabetic animal with implant in the 3rd Group-A gained 57 g, and the other diabetic animal in the 3rd Group-B gained 82 g during the time when the implant was functional for about 40 days. The healthy control animal in the 1st Group gained body weight steadily as expected, but the diabetic control in the 2nd Group lost 45 g after 38 days and it appeared emaciated as well as stunted.

Hyperglycemia recurred on the 32nd day of the calculated 40-day service life of the ⅛ disc implanted in the diabetic rat of the 3rd Group-A. For the ¼ disc in the 3rd Group-B of another diabetic animal, the preparation implanted functioned well until the 40th day of the calculated 80-day supply of insulin. Since the blood glucose values monitored over the period were lower than the healthy control group, the implants in the 3rd Group of diabetic animals might have received more than the postulated 3 IU/day which would account for the shorter service life actually observed. Since the implant in the animal of the 3rd Group-B was double in size as compared to the other without showing ill effects, the results also demonstrated the margin of safety in the use of the implant. At biopsy to retrieve the implant, no fibrous tissue encapsultion was evident, and the previously distinct edges of the plant made of palmitic acid was found to have been rounded by erosion. In 1 animal, the spent implant had broken into several small pieces. Analyses by solid phase radioimmunoassay showed that there was only trace amount of insulin remaining in the recovered lipid remnants.

EXAMPLE 2

An amount of 170 mg cholesterol powder is mixed with 30 mg of bovine insulin powder (24 IU/mg) and compressed into a pellet disc at 2.5 metric tons essentially as described in Example 1. Therefore, this pellet disc contains 15% insulin by weight. The disc is cut evenly into 8 pieces, and 2 pieces are inserted subcutaneously near the abdomen of each of 3 streptozotocin-induced diabetic Wistar rats of comparable body weight. The blood glucose level shown in Table 2 is monitored by Dextrostix® and the Glucometer®. Food and water are available to the animals ad libitum.

TABLE 2

Reproducibility of Hyperglycemia Reduction by the Pellet Disc Pieces

| Duration | Blood Glucose (mM/L) | | |
|---|---|---|---|
| (Days) | 1st Rat | 2nd Rat | 3rd Rat |
| (diabetic with no disc) | | | |
| 0 | >22 | >22 | >22 |
| (24 hr after ¼ disc inserted) | | | |
| 1 | 14.5 | 2.8 | 3.4 |
| 3 | 5.1 | 4.4 | 2.9 |
| 6 | 3.0 | 3.9 | 4.1 |
| 10 | 4.2 | 11.4 | 3.0 |
| 14 | 3.3 | 4.1 | 2.7 |
| 17 | 20.3 | 3.0 | 2.2 |
| 20 | >22 | 3.2 | 21.5 |
| 23 | >22 | 5.7 | >22 |
| 26 | >22 | 3.2 | >22 |
| 29 | — | >22 | — |
| 32 | — | >22 | >22 |
| 35 | >22 | >22 | — |

The data demonstrate that there is similar hyperglycemia reduction in all 3 diabetic animals up to day 14 at least. But in the 2nd rat, it continued for about 12 more days, and at least 3 extra days for the 3rd rat. Therefore, the pieces from the same pellet disc can provide reproducible reduction in hyperglycemia, while the duration may vary in different animals. All 3 rats sustained growth in body weight during the functional period of the implant.

The ⅛ pieces of pellet disc were retrieved from the diabetic animals after 35 days and analyzed for residual insulin. After cleaning, the pieces were crushed in 50 ml of phosphate buffered saline which was warmed to 40° C. to enhance the extraction of the insulin quantitatively. After the appropriate dilution of this solution, analyses by solid phase radioimmunoassay show that there is negligible amount of insulin remaining.

EXAMPLE 3

A 200-mg pellet disc containing 30% bovine insulin in stearic acid, is cut evenly into four ¼ pieces. Two pieces are then implanted subcutaneously near the abdomen of an alloxan-induced (200 mg/kg body weight) diabetic male New Zealand White rabbit of body weight 3.1 kg and blood glucose content at >22 mM/L for 2.5 weeks. The blood glucose is monitored the day after insertion of the ¼ pellet disc, and then in the intervals shown in Table 3 below. On 2 occasions, the ¼ pellet disc implant is taken out then later re-inserted. A normal non-diabetic rabbit has a range of 5.1 to 6.3 mM glucose/L blood when monitored on alternate days in a 2-week period. Food and water are available ad libitum as usual. The changes in blood glucose level with insertion and removal are given in Table 3.

TABLE 3

Dependence of Blood Glucose on the Presence of Insulin-Containing Lipid Pellet Disc in DiabeticRabbit

| Duration (days) | Blood Glucose (mM/L) |
|---|---|
| (no disc) | |
| 0 | >22 |
| (24 hr after disc inserted) | |
| 1 | 7.8 |
| 3 | 4.7 |
| 9 | 5.8 |
| 12 | 5.0 |
| (removed disc) | |
| 13 | 18.7 |
| 14 | >22 |
| 17 | >22 |
| 20 | >22 |
| (re-insert same disc) | |
| 21 | 6.5 |
| 23 | 5.1 |
| 26 | 4.3 |
| 30 | 4.7 |
| (remove disc again) | |
| 31 | 21.1 |
| 32 | >22 |
| 34 | >22 |
| 36 | >22 |
| (insert same disc again) | |
| 38 | 4.4 |
| 41 | 5.0 |
| 45 | 6.2 |
| 50 | 6.8 |

The data presented above unequivocally demonstrate the dependence of blood glucose change of the diabetic rabbit on the insulin containing preparation of the present invention. As well, during the alternating period, the body weight of the rabbit was observed to increase when the functional implant was in place, but a decrease of as much as 175 g in body weight could be detected within 24 hr upon removal of the implant. In addition, the activity of the labile insulin in the ¼ pellet disc does not seem to be affected by the in vivo and ex vivo alternation providing that the retrieved pellet disc segment is preserved in a sterile container and refrigerated. When the ¼ pellet disc is in the body of the diabetic rabbit, normoglycemia is maintained to a remarkable consistency.

EXAMPLE 4

An amount of 150 mg palmitic acid, 20 mg glyceryl tripalmitate, and 30 mg porcine insulin (24 IU/mg) are mixed thoroughly in the plastic weighing boat, and then in a capped polyethylene tube on the vortex mixer. The fine powder admixture is compressed into a standard size pellet disc essentially as described in Example i, except at 3 metric tons for 5 min. The smooth pellet disc is cut on a Teflon® slab into chips of approximately $1 \times 1 \times 1$ mm$^3$ with a utility knife. The chips are picked up individually with a pair of tweezers and briefly dipped in a small amount of water to wash off any adhering powder. Several pieces of the chip are transferred to a small plastic weighing boat and about 25 mg of the total is taken for subcutaneous insertion near the abdomen of a diabetic Wistar rat (body weight: 350 g) by a trocar needle. The weight of the chips corresponds to about ⅛ of the original standard sized pellet disc and should have an insulin content of about 4 mg. This amount of insulin has a total activity of about 100 IU. At a demand of about 3 IU/day, it is expected to reduce hyperglycemia in the diabetic rat for 33 days. The test animal is bled according to the schedule shown in Table 4, and the Glucometer® method is used to determine the glucose level as in Example 1.

TABLE 4

Lowering of Blood Glucose in Diabetic Rat by Inserted Insulin Containing Chips

| Duration (days) | Blood Glucose (mM/L) |
|---|---|
| (no chips inserted) | |
| 0 | >22 |
| (chips inserted) | |
| 1 | 3.0 |
| 2 | 2.4 |
| 3 | 2.7 |
| 4 | 3.0 |
| 7 | 2.8 |
| 10 | 3.8 |
| 15 | 3.1 |
| 21 | 2.9 |
| 28 | 2.9 |
| 34 | 3.2 |
| 36 | 3.4 |
| 40 | 20.1 |
| 47 | >22 |
| 50 | >22 |

The results obtained show that even when the pellet disc is sub-divided into fragments, there is no unexpected overdose of the incorporated insulin. The same hyperglycemia reduction is again achieved in comparison to the larger pieces of the pellet disc as described in Example 1. However, the longer duration of maintenance does not appear to be entirely consistent with the data for the ⅛ pellet disc given in Table 1 of Example 1. The difference further indicates the complexity of the on-going process involving erosion, as well as insulin availability, demand, absorption and its inactivation which apparently vary among the test animals. In addition, the more expensive porcine insulin used herein is known to be less immunogenic than the similar polypeptide hormone of bovine origin, and perhaps less prone to plexing with antibodies. At biopsy on day 50, only small round remnants of the inserted chips could be found, indicating absorption had occurred. Further, this animal grew by 117 g during the 40-day period of therapy.

EXAMPLE 5

An amount of 110 mg palmitic acid, 20 mg cholesterol, 30 mg stearic acid, and 40 mg porcine growth hormone somatotropin powder is mixed thoroughly and compressed into a pellet disc at 3 metric tons for 3 min. as otherwise outlined in Example 1. The disc is cut into quadrants, and dropped into a stirred flask containing 1 L of bicarbonate buffer at pH 8 with 0.1% sodium azide as preservative. Aliquots are withdrawn twice weekly for analyses of protein content by the Coomassie dye method described in Example 1. The increasing amount of the polypeptide hormone in the solution is shown in Table 5 below.

TABLE 5

Cumulative Amount of Somatotropin in Solution Derived from Pieces of Pellet Disc

| Duration (days) | Hormone in Solution (mg/L) |
|---|---|
| 1 | 1.1 |
| 3 | 3.8 |
| 5 | 6.0 |
| 8 | 9.2 |
| 10 | 10.9 |
| 12 | 13.0 |
| 15 | 17.5 |
| 17 | 18.2 |
| 19 | 21.1 |
| 22 | 25.0 |
| 24 | 26.1 |
| 26 | 27.4 |
| 29 | 31.3 |
| 31 | 34.9 |
| 34 | 36.5 |
| 36 | 36.1 |
| 40 | 36.4 |

The results showed that >90% of the polypeptide hormone entered the stirred solution gradually for a period of over 4 weeks. If more somatotropin is required daily, additional pieces may be used or its content in the pellet disc can be slightly increased. For implantation to promote growth, no antigenic problem will develop if the preparation is used in an homologous recipient, especially when the excipient components chosen are natural lipid materials present in all tissues.

From the preceding examples, it is thus seen that the objects set forth above are efficiently attained. Since changes may be made in carrying out the above described process and in the article set forth without departing from the scope of the invention, it will be understood that the above examples are illustrative only, and the invention is not limited thereto.

I claim:

1. A bioerodible preparation implant with sustained action which consists of a compressed admixture of an effective amount of solid bioactive polypeptide with lipid powder, with the said lipid powder being selected from the group consisting of glycerides, waxes, long-chain fatty acids or derivatives, phospholipids, sphingolipids, cerebrosides, terpenes, non-hormonal steroids or a combination thereof.

2. A bioerodible preparation with sustained action which continuously reduces diabetic hyperglycemia for a prolonged period of time and promotes growth upon implantation consisting of a compressed admixture of insulin powder with a lipid powder, with the said lipid powder being selected from the group consisting of glycerides, waxes, long-chain fatty acids or derivatives, phospholipids, sphingolipids, cerebrosides, terpenes, non-hormonal steroids or a combination thereof.

3. A bioerodible preparation of claim 2 wherein the amount of insulin is about 11% to about 40% by weight of said admixture.

4. A bioerodible preparation of claim 3 which is a pellet disc or fraction thereof, rod, chip, sphere or flake.

5. A kit for preparing a bioerodible preparation as claimed in claim 3 which consists of insulin and the lipid material in a container therefore.

6. A bioerodible preparation of claim 3 wherein the lipid is a glyceride selected from the group consisting of glyceryl esters of lauric, myristic, palmitic, stearic, oleic, or linoleic acids or a combination thereof.

7. A bioerodible preparation of claim 3 wherein the lipid is a long-chain fatty acid or derivative selected from the group consisting of lauric, myristic, palmitic, stearic, oleic, or linoleic acids, their simple esters, salts, amides, anhydrides, or a combination thereof.

8. A bioerodible preparation of claim 3 wherein the lipid is a non-hormonal steroid selected from the group consisting of coprostanol, cholesterol, cholic acid, their esters, simple glycosides or a combination thereof.

9. A method of treating diabetes mellitus which comprises continuously reducing hyperglycemia by implantation of a compressed powder admixture consisting of an effective amount of insulin and lipid powder selected from the group consisting of glycerides, waxes, long-chain fatty acids or derivatives, phospholipids, sphingolipids, cerebrosides, terpenes, non-hormonal steroids or a combination thereof.

10. A method of treating diabetes as claimed in claim 9 wherein the amount of insulin comprises 11% to 40% by weight of said admixture.

11. A method of treating diabetes as claimed in claim 9 wherein the lipid is a glyceride selected from the group consisting of glyceryl esters of lauric, myristic, palmitic, stearic, oleic, or linoleic acids or a combination thereof.

12. A method of treating diabetes as claimed in claim 9 wherein the lipid is a long-chain fatty acid or derivative selected from the group consisting of lauric, myristic, palmitic, stearic, oleic, or linoleic acids, their simple esters, salts, amides, anhydrides or a combination thereof.

13. A method of treating diabetes as claimed in claim 9 wherein the lipid is a non-hormonal steroid selected from the group consisting of coprostanol, cholesterol, cholic acid, their esters, simple glycosides or a combination thereof.

14. A bioerodible preparation of claim 1 with sustained action wherein said bioactive polypeptide is somatotropin.

15. A bioerodible preparation of claim 14 wherein the amount of somatotropin comprises about 1% to about 50% by weight of the admixture and the lipid is selected from the group consisting of glycerol esters of lauric, myristic, palmitic, stearic, oleic, or linoleic acids or a combination thereof; lauric, myristic, palmitic, stearic, oleic, or linoleic acids, their simple esters, salts, amides, anhydrides, or a combination thereof; and coprostanol, cholesterol, choleic acid, their esters, simple glycosides or a combination thereof.

16. A bioerodible preparation of claim 15 which is a pellet disc or fraction thereof, rod, chip, sphere or flake.

17. A kit for preparing a bioerodible preparation as claimed in claim 15 which consists of the somatropin and the lipid in a container.

* * * * *